United States Patent [19]

Lee

[11] Patent Number: 5,079,233
[45] Date of Patent: Jan. 7, 1992

[54] N-ACYL DERIVATIVES OF THE LL-E33288 ANTITUMOR ANTIBIOTICS, COMPOSITION AND METHODS FOR USING THE SAME

[75] Inventor: May D. M. Lee, Monsey, N.Y.

[73] Assignee: American Cyanamid Company, Stamford, Conn.

[21] Appl. No.: 338,928

[22] Filed: Apr. 14, 1989

Related U.S. Application Data

[63] Continuation-in-part of Ser. No. 4154, Jan. 30, 1987, Pat. No. 5,037,651.

[51] Int. Cl.⁵ .................. A61K 31/70; C07H 15/00
[52] U.S. Cl. ........................................ 514/25; 514/53; 536/16.8; 536/17.5; 536/17.6; 536/18.1; 536/18.5
[58] Field of Search ............... 536/16.8, 17.2, 17.6, 536/18.1, 18.5; 514/25, 53

[56] References Cited

U.S. PATENT DOCUMENTS 4,065,615 12/1977 Horii et al. ................. 536/13.3

Primary Examiner—Johnnie R. Brown
Assistant Examiner—Elli Peselev
Attorney, Agent, or Firm—H. G. Jackson

[57] ABSTRACT

The invention is N-acyl and dihydro-N-acyl analogs of the family of antibacterial and antitumor agents known collectively as the E33288 complex.

18 Claims, 8 Drawing Sheets

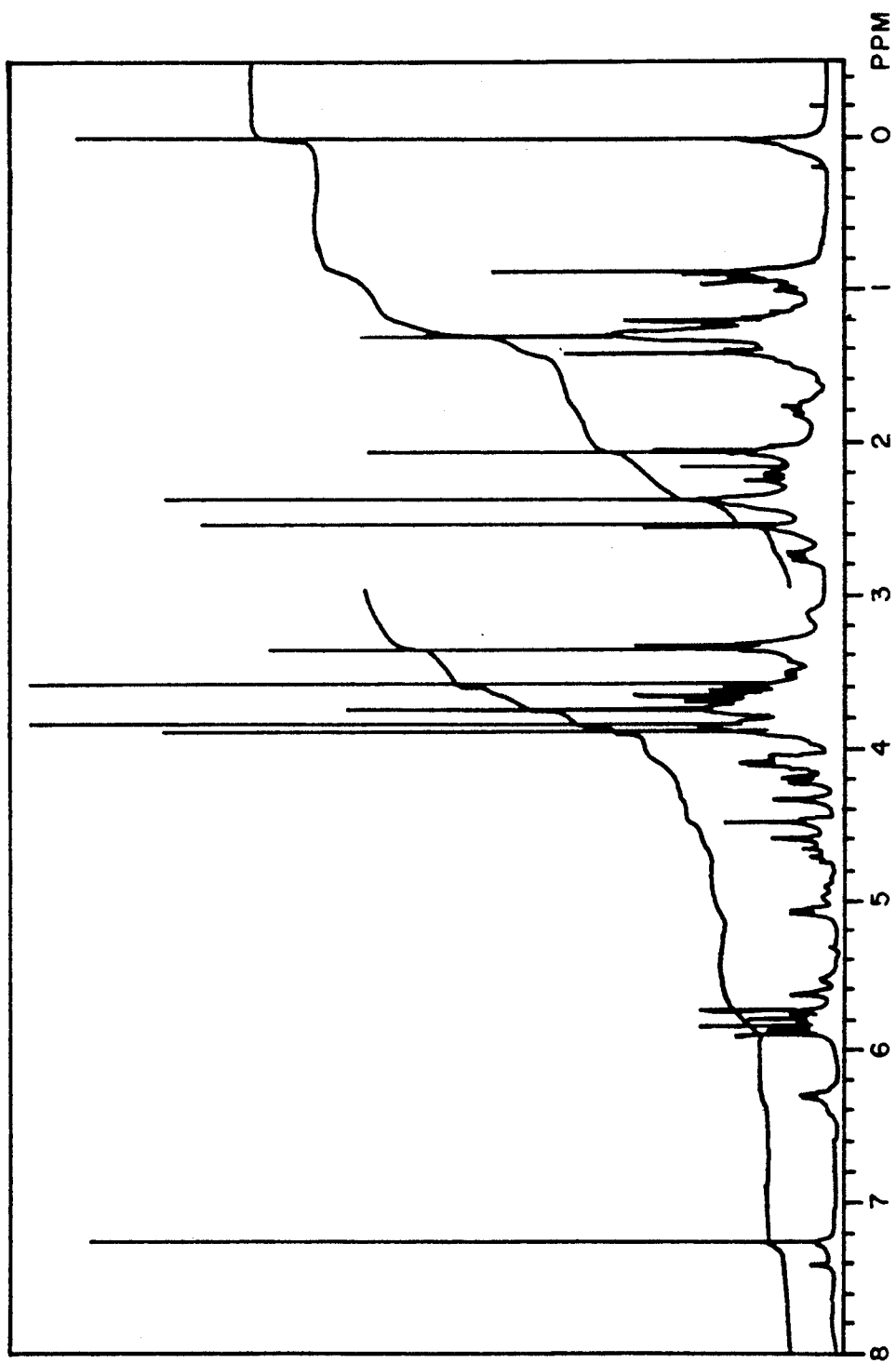

1

N-ACYL DERIVATIVES OF THE LL-E33288 ANTITUMOR ANTIBIOTICS, COMPOSITION AND METHODS FOR USING THE SAME

This is a continuation-in-part application, of copending Ser. No. 004,154, filed Jan. 30, 1987 now U.S. Pat. No. 5,037,651.

SUMMARY OF THE INVENTION

The invention describes the N-acyl derivatives of the $\alpha_2{}^{Br}$, $\beta_1{}^{Br}$, $\gamma_1{}^{Br}$, $\alpha_2{}^{I}$, $\beta_1{}^{I}$, $\gamma_1{}^{I}$, and $\delta_1{}^{I}$ components and of the N-acyl-dihydro derivatives of the $\alpha_2{}^{Br}$, $\beta_1{}^{Br}$, $\gamma_1{}^{Br}$, $\alpha_2{}^{I}$, $\beta_1{}^{I}$, $\gamma_1{}^{I}$, and $\delta_1{}^{I}$ components of the LL-E33288 antibiotic complex prepared by reacting the antibiotic with an unsubstituted or substituted acid anhydride acyl cation equivalent or acid chloride. These N-acyl derivatives are effective antibacterial and antitumor agents.

BRIEF DESCRIPTION OF THE DRAWINGS

Figure I: The proton magnetic resonance spectrum of N-acetyl-LL-E33288$\delta_1{}^{I}$.

Figure II: The proton magnetic resonance spectrum of N-formyl-LL-E33288$\delta_1{}^{I}$.

Figure 1:
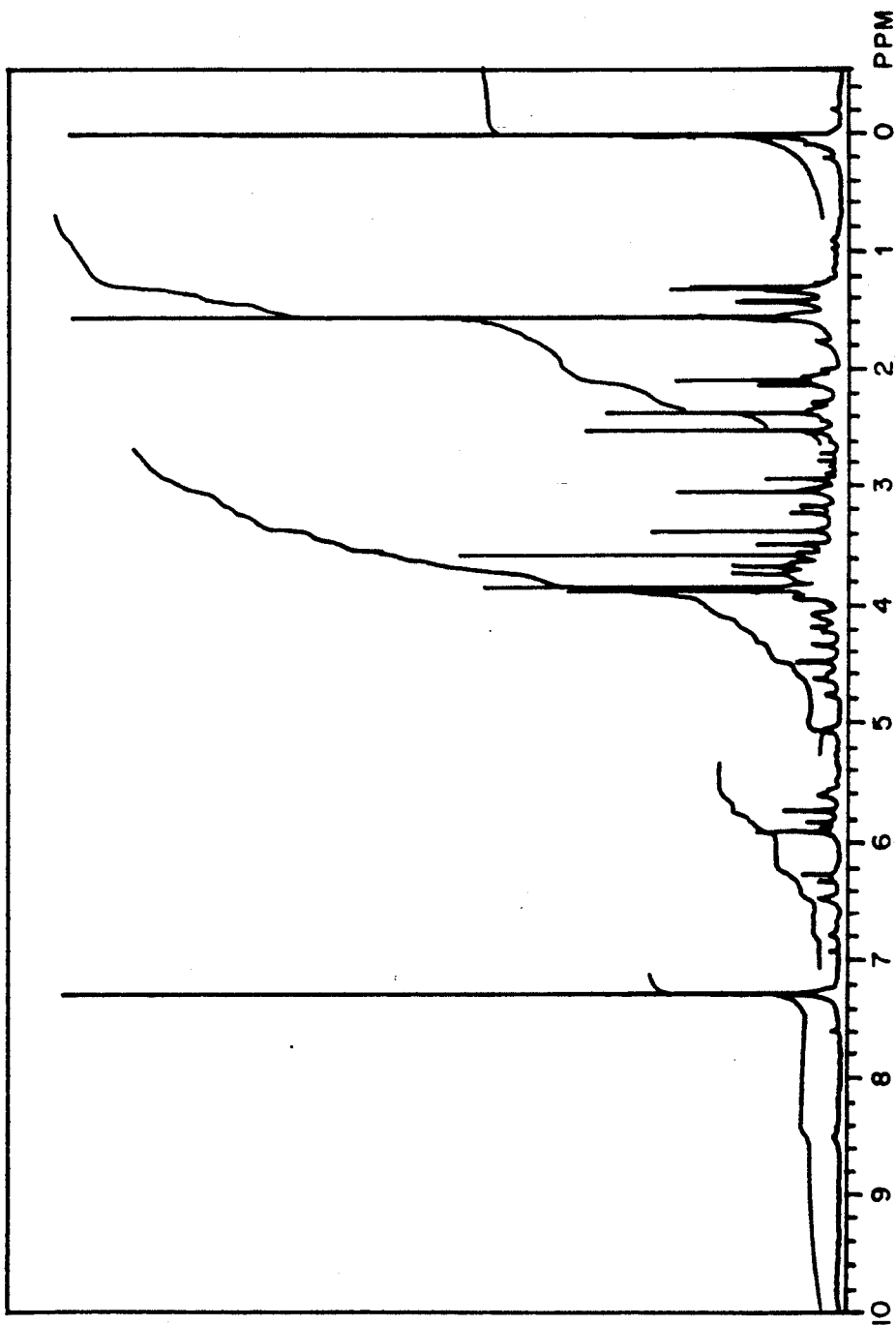
Figure 2:
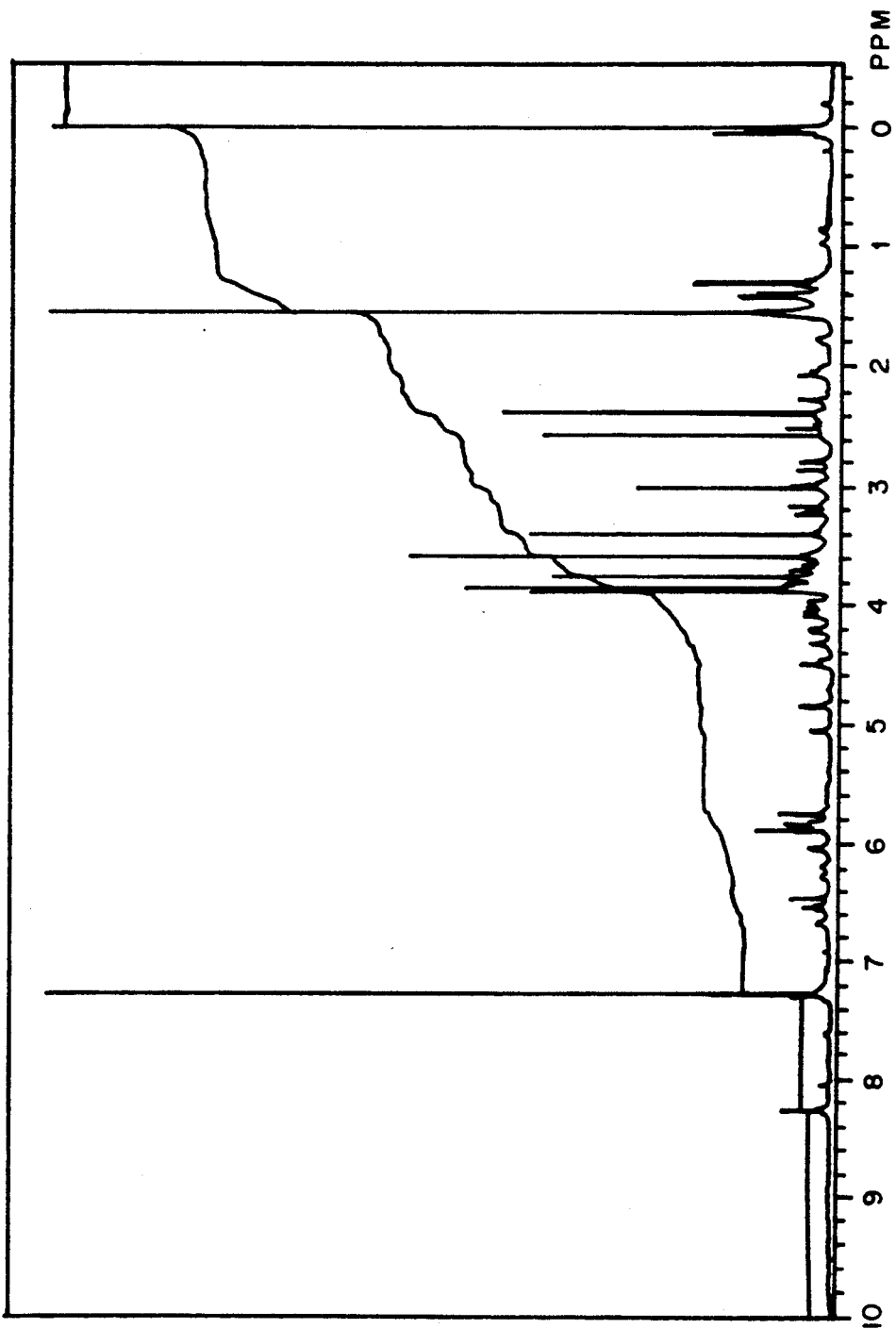
Figure 3:
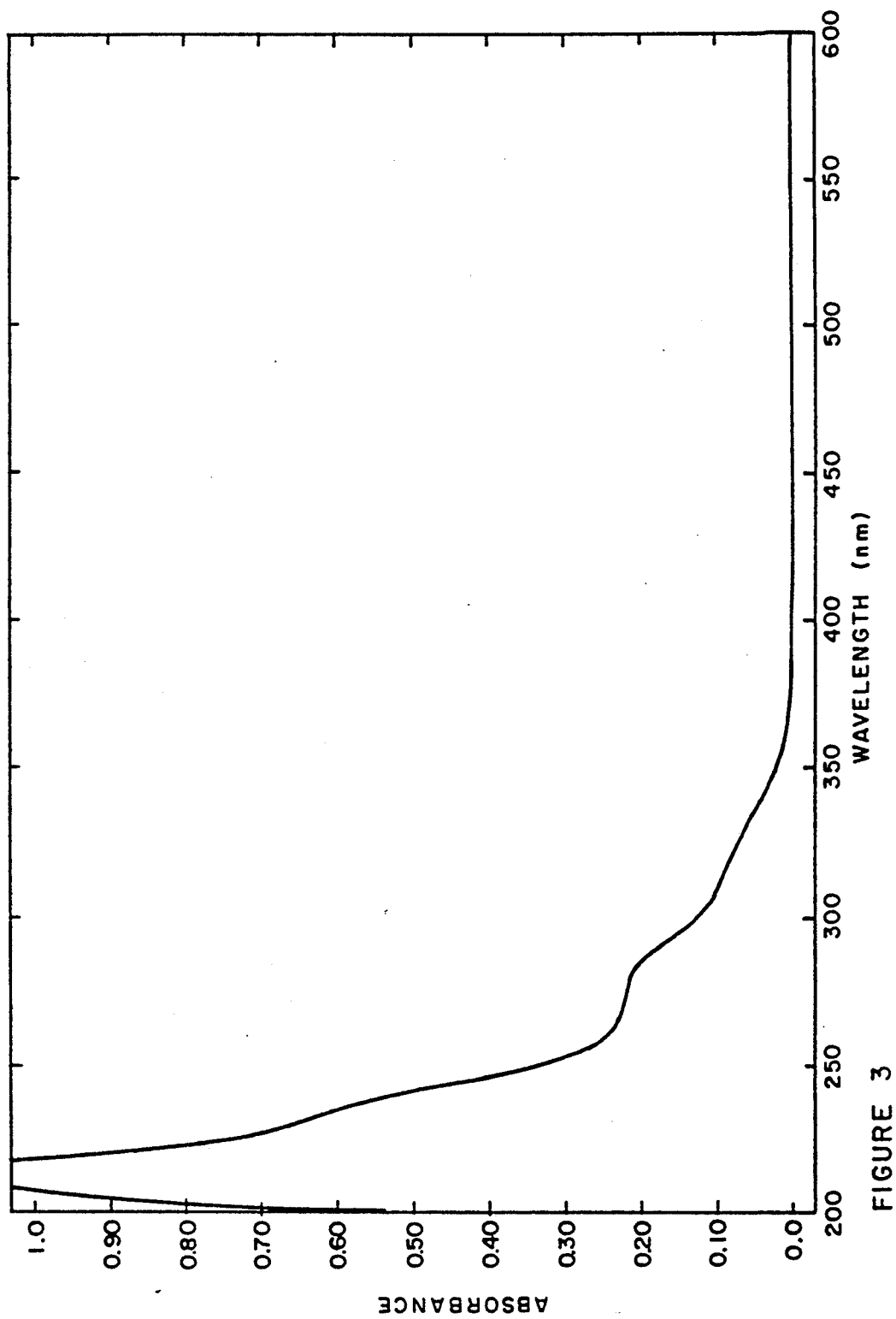
Figure 4:
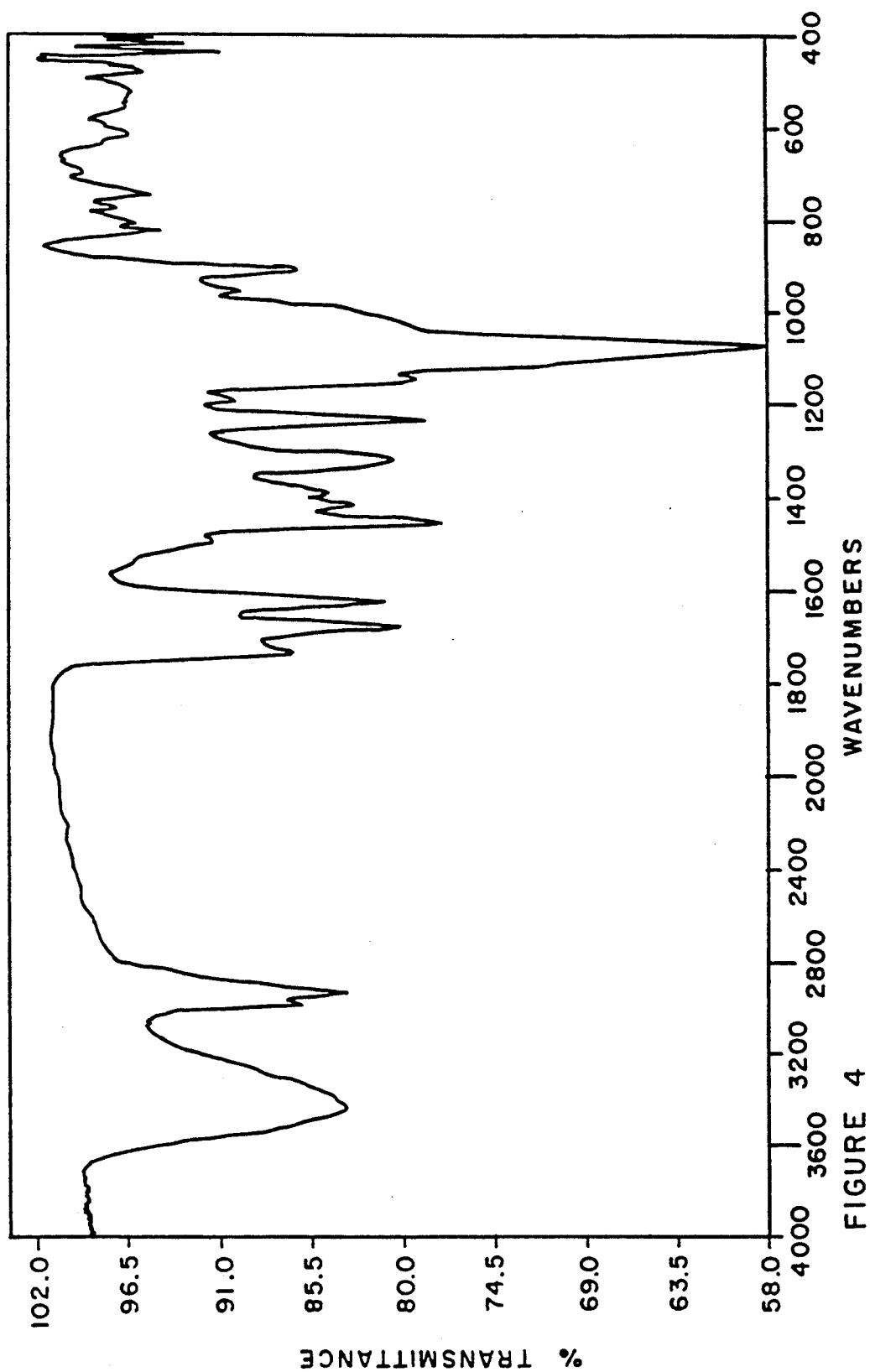
Figure 5:
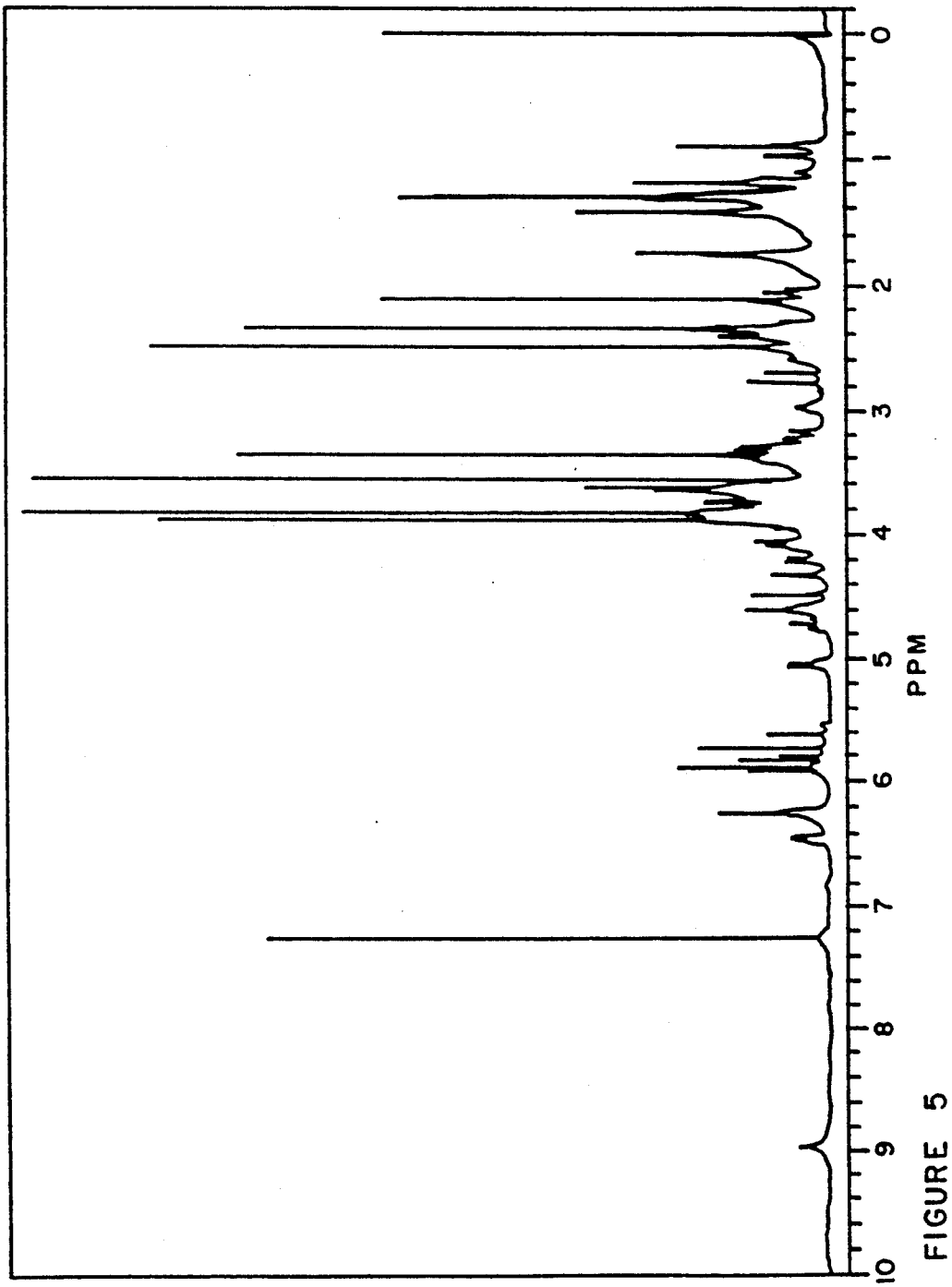
Figure 6:
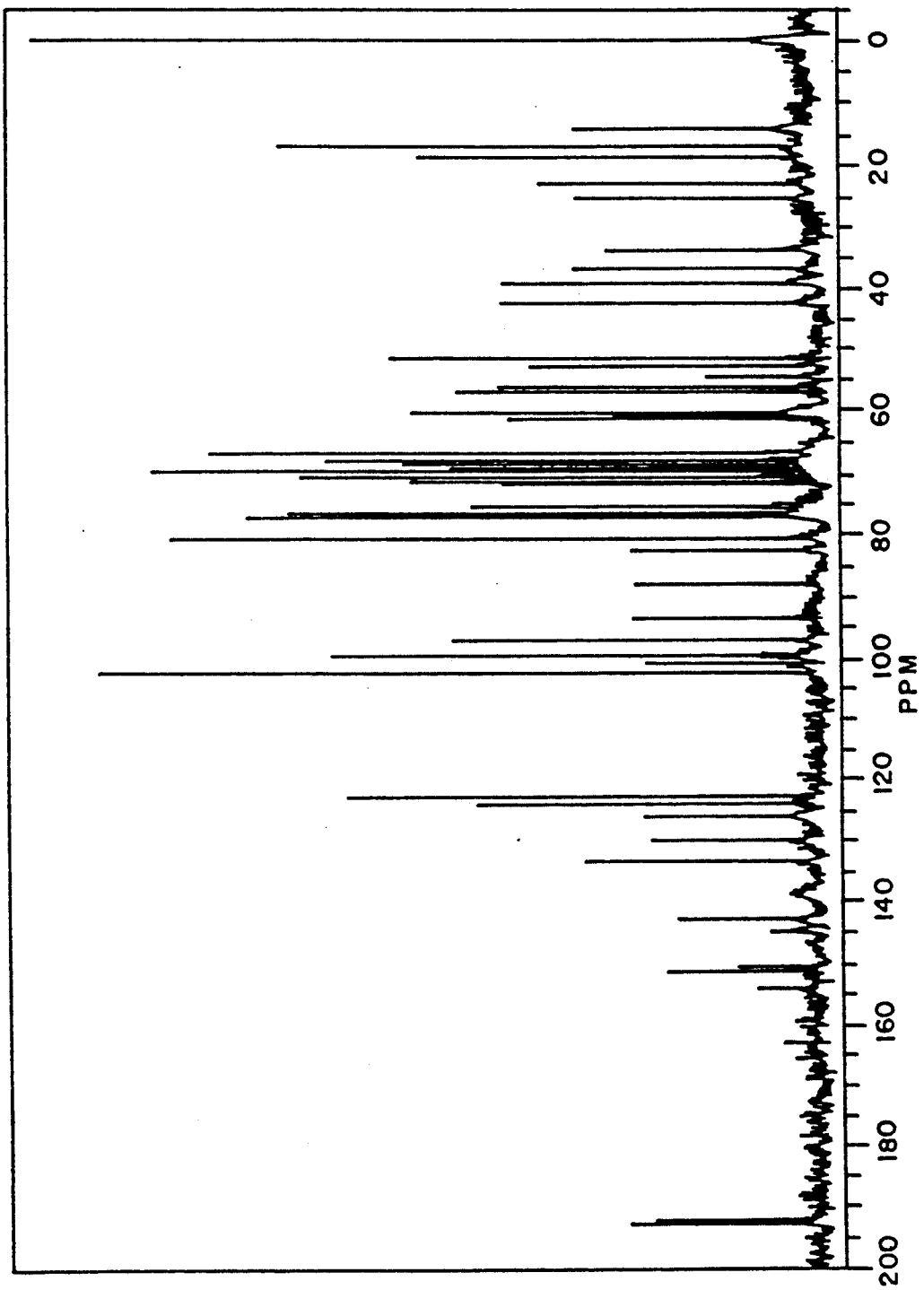
Figure 7:
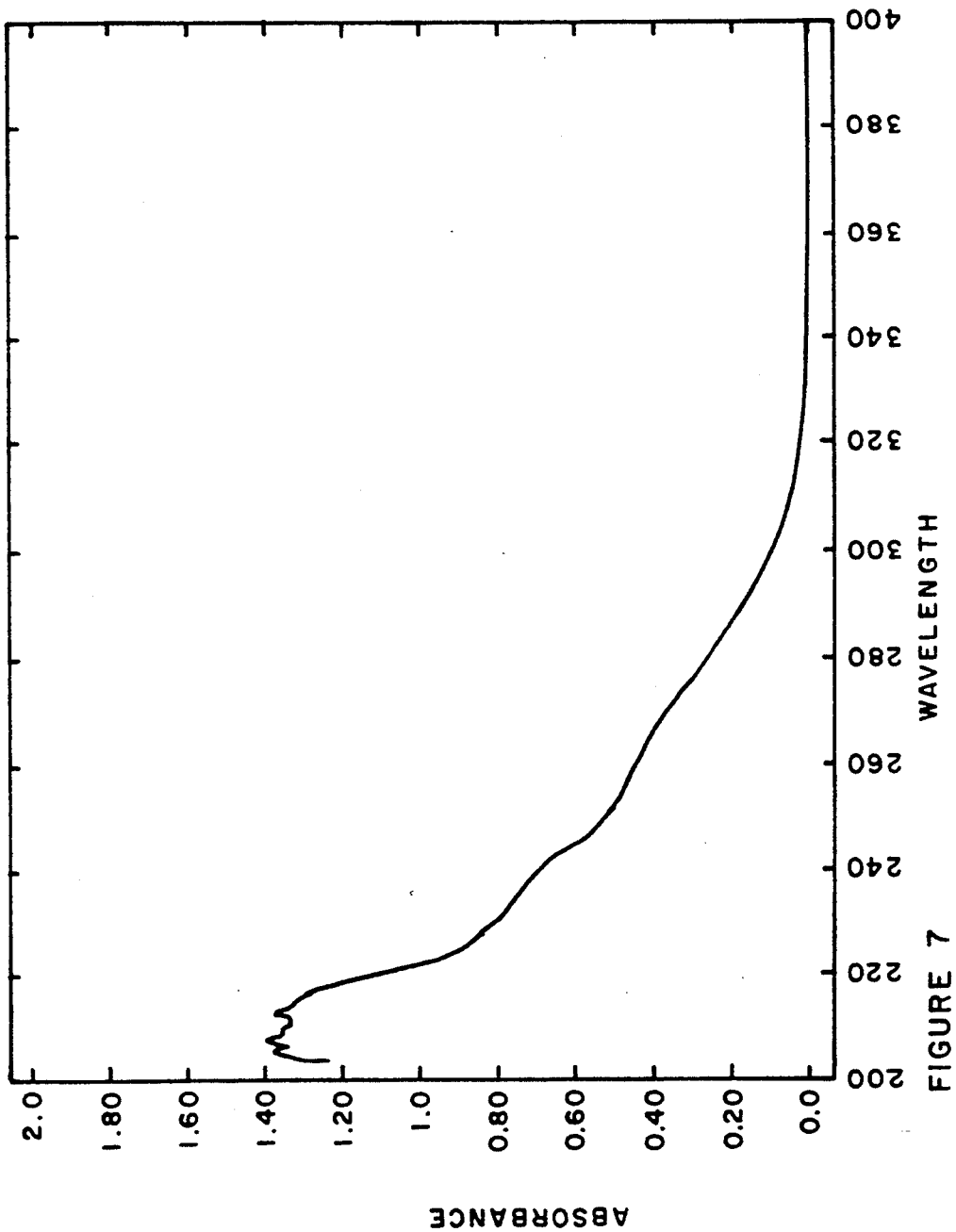

Figure III: The ultraviolet absorption spectrum of N-acetyl-LL-E33288$\gamma_1{}^{I}$.

Figure IV: The infrared absorption spectrum of N-acetyl-LL-E33288$\gamma_1{}^{I}$.

Figure V: The proton magnetic resonance spectrum of N-acetyl-LL-E33288$\gamma_1{}^{I}$.

Figure VI: The carbon-13 magnetic resonance spectrum of N-acetyl-LL-E33288$\gamma_1{}^{I}$.

Figure VII: The ultraviolet absorption spectrum of N-acetyl-dihydro-LL-E33288$\gamma_1{}^{I}$.

Figure VIII: The proton magnetic resonance spectrum of N-acetyl-dihydro-LL-E33288$\gamma_1{}^{I}$.

DETAILED DESCRIPTION OF THE INVENTION

The family of antibacterial and antitumor agents, known collectively as the LL-E33288 complex, are described and claimed in copending U.S. Patent Application Ser. No. 009,321, filed Jan. 30, 1987 now U.S. Pat. No. 4,970,198 and are used to prepare the N-acyl derivatives of this invention. The above application describes the LL-E33288 complex, the components thereof, namely, LL-E33288$\alpha_1{}^{Br}$, LL-E33288$\alpha_2{}^{Br}$, LL-E33288$\alpha_3{}^{Br}$, LL-E33288$\alpha_4{}^{Br}$, LL-E33288$\beta_1{}^{Br}$, LL-E33288$\beta_2{}^{Br}$, LL-E33288$\gamma_1{}^{Br}$, LL-E33288$\alpha_1{}^{I}$, LL-E33288$\alpha_2{}^{I}$, LL-E33288$\alpha_3{}^{I}$, LL-E33288$\beta_1{}^{I}$, LL-E33288$\beta_2{}^{I}$, LL-E33288$\gamma_1{}^{I}$, and LL-E33288$\delta_1{}^{I}$, and methods for their production by aerobic fermentation utilizing a new strain of *Micromonospora echinospora* ssp. *calichensis* or natural or derived mutants thereof. The proposed chemical structures of some of the above named components are disclosed in Ser. No. 009,321 now U.S. Pat. No. 4,970,198 and are reproduced in Table I below.

TABLE I

Proposed Structures for the LL-E33288 Components

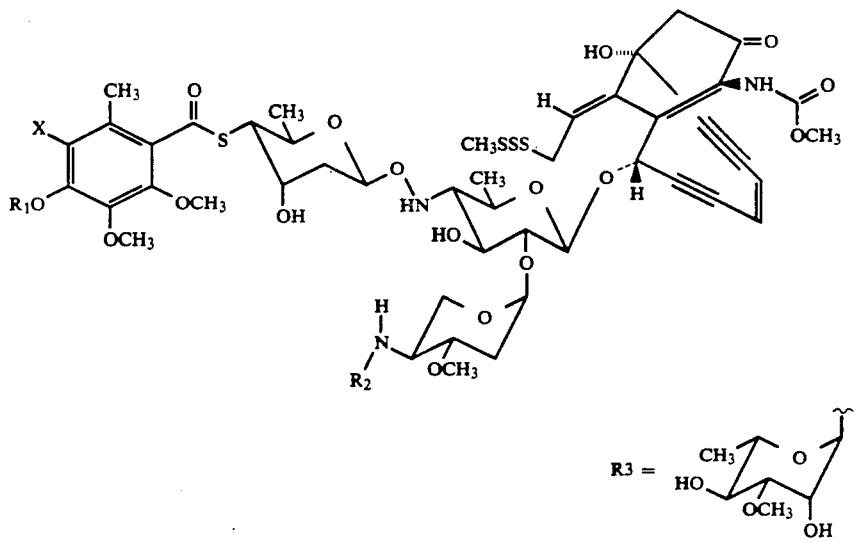

| Designation | $R_1$ | $R_2$ | X |
|---|---|---|---|
| E33288$\alpha_2{}^{I}$ | H | $C_2H_5$ | I |
| E33288$\beta_1{}^{I}$ | $R_3$ | $(CH_3)_2CH$ | I |
| E33288$\gamma_1{}^{I}$ | $R_3$ | $C_2H_5$ | I |
| E33288$\delta_1{}^{I}$ | $R_3$ | $CH_3$ | I |
| E33288$\alpha_2{}^{Br}$ | H | $C_2H_5$ | Br |
| E33288$\beta_1{}^{Br}$ | $R_3$ | $(CH_3)_2CH$ | Br |
| E33288$\gamma_1{}^{Br}$ | $R_3$ | $C_2H_5$ | Br |

As can be seen from the structures disclosed in Table I, the $\alpha_2{}^{Br}$, $\beta_1{}^{Br}$, $\gamma_1{}^{Br}$, $\alpha_2{}^{I}$, $\beta_1{}^{I}$, $\gamma_1{}^{I}$, and $\delta_1{}^{I}$ components of the LL-E33288 antibiotic complex each contain a secondary amino group which is part of a substituted 4-aminopentose unit. It has now been discovered that the reaction of any of the above components with an unsubstituted or substituted, saturated or unsaturated alkyl or aryl acid anhydride, acid chloride or acyl cation equivalent results in the introduction of an acyl moiety on the secondary amino group as shown in Scheme I below.

Scheme 1

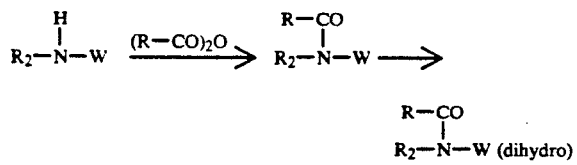

wherein W is the substituent attached to $R_2NH-$ of the aminopentose in Table I, R is hydrogen or a branched or unbranched alkyl ($C_1-C_{10}$) or alkylene ($C_1-C_{10}$) group, an aryl or heteroaryl group, or an aryl-alkyl ($C_1-C_5$) or heteroaryl-alkyl ($C_1-C_5$) group, all optionally substituted by one or more hydroxy, amino, carboxy, halo, nitro, lower ($C_1-C_3$) alkoxy, or lower ($C_1-C_5$) thioalkoxy groups.

N-Acyl derivatives are also prepared from the dihydro derivatives of the LL-E33288 antibiotics, namely dihydro-LL-E33288$\alpha_2^{Br}$, dihydro-LL-E33288$\beta_1^{Br}$, dihydro-E33288$\gamma_1^{Br}$, dihydro-LL-E33288$\alpha_2^I$, dihydro-LL-E33288$\beta_1^I$, dihydro-LL-E33288$\gamma_1^I$, and dihydro-LL-E33288$\delta_1^I$, of parent application Ser. No. 004,154 now U.S. Pat. No. 5,037,651.

As an example, reaction of LL-E33288$\gamma_1^I$ with acetic anhydride in methanol produces N-acetylLL-E33288$\gamma_1^I$ while the reaction of LL-E33288$\delta_1^I$ with the mixed anhydride of acetic acid and formic acid produces N-formyl-LL-E33288$\delta_1^I$, both potent new antitumor antibiotics. The reaction of dihydro-LL-E33288$\gamma_1^I$ with acetic anhydride in methanol produces N-acetyl-dihydro-LL-E33288$\gamma_1^I$. N-Acetyl-dihydro-LL-E33288$\gamma_1^I$ is also produced by the reaction of N-acetyl-LL-E33288$\gamma_1^I$ with sodium borohydride under the conditions described in Ser. No. 004,154. Some of the chemical structures of the N-Acyl derivatives of the LL-E33288 and the dihydro-LL-E33288 anticancer antibiotics are shown in Table II below:

TABLE II
Proposed Structures for the N-Acyl Derivatives of the LL-E33288 and dihydro LL-E33288 Antibiotics

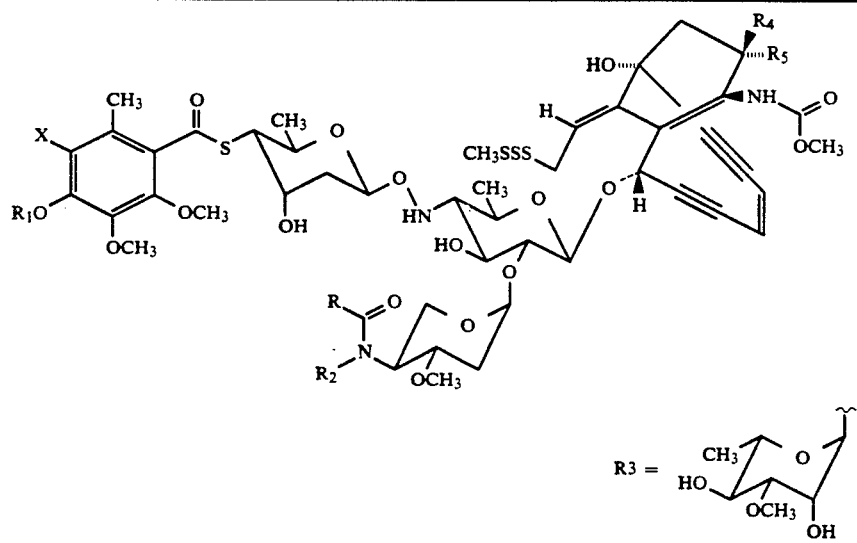

| Designation | $R_1$ | $R_2$ | $R_4$ | $R_5$ | X |
|---|---|---|---|---|---|
| N-Acyl-dihydro LL-E33288$\alpha_2^I$ | H | $C_2H_5$ | OH | H | I |
| N-Acyl LL-E33288$\alpha_2^I$ | H | $C_2H_5$ | | =O | I |
| N-Acyl-dihydro LL-E33288$\beta_1^I$ | $R_3$ | $(CH_3)_2CH$ | OH | H | I |
| N-Acyl LL-E33288$\beta_1^I$ | $R_3$ | $(CH_3)_2CH$ | | =O | I |
| N-Acyl-dihydro LL-E33288$\gamma_1^I$ | $R_3$ | $C_2H_5$ | OH | H | I |
| N-Acyl LL-E33288$\gamma_1^I$ | $R_3$ | $C_2H_5$ | | =O | I |
| N-Acyl-dihydro LL-E33288$\delta_1^I$ | $R_3$ | $CH_3$ | OH | H | I |
| N-Acyl LL-E33288$\delta_1^I$ | $R_3$ | $CH_3$ | | =O | I |
| N-Acyl-dihydro LL-E33288$\alpha_2^{Br}$ | H | $C_2H_5$ | OH | H | Br |
| N-Acyl LL-E33288$\alpha_2^{Br}$ | H | $C_2H_5$ | | =O | Br |
| N-Acyl-dihydro LL-E33288$\beta_1^{Br}$ | $R_3$ | $(CH_3)_2CH$ | OH | H | Br |
| N-Acyl LL-E33288$\beta_1^{Br}$ | $R_3$ | $(CH_3)_2CH$ | | =O | Br |
| N-Acyl-dihydro LL-E33288$\gamma_1^{Br}$ | $R_3$ | $C_2H_5$ | OH | H | Br |
| N-Acyl LL-E33288$\gamma_1^{Br}$ | $R_3$ | $C_2H_5$ | | =O | Br |

R = hydrogen or a branched or unbranched alkyl ($C_1-C_{10}$) or alkylene ($C_1-C_{10}$) group, an aryl or heteroaryl group, or an aryl-alkyl ($C_1-C_5$) or heteroaryl-alkyl ($C_1-C_5$) group, all optionally substituted by one or more hydroxy, amino, carboxy, halo, nitro, lower ($C_1-C_3$) alkoxy, or lower ($C_1-C_5$) thioalkoxy groups.

The physico-chemical characteristics of four of the N-acyl derivatives of the LL-E33288 antitumor antibiotics, namely, N-acetyl-LL-E33288$\delta_1^I$, N-formyl-LL-E33288$\gamma_1^I$, N-acetyl-LL-E33288$\gamma_1^I$ and N-acetyl-dihydro-LL-E33288$\gamma_1^I$ are described below. N-acetyl-LL-E33288$\delta_1^I$ a) molecular weight: 1395, determined by FABMS:
b) molecular formula: $C_{56}H_{74}N_3O_{22}IS_4$, exact mass for M+K was determined by high resolution FABMS to be 1434.2329 for $C_{56}H_{74}N_3O_{22}IS_4K$; and
c) proton magnetic resonance spectrum: as shown in Figure I (300 MHz, CDCl$_3$)

N-formyl-LL-E33288$\delta_1^I$ a) molecular weight: 1381, determined by FABMS;
b) molecular formula: $C_{55}H_{72}N_3O_{22}IS_4$, exact mass for M+K was determined by high resolution FABMS to be 1420.2172 for $C_{55}H_{72}N_3O_{22}IS_4K$; and
c) proton magnetic resonance spectrum: as shown in Figure II (300 MHz, CDCl$_3$).

N-acetyl-LL-E33288$\gamma_1^I$ a) molecular weight: 1409, determined by FABMS;
b) molecular formula: $C_{57}H_{76}N_3O_{22}IS_4$, exact mass for M+H was determined by high resolution FABMS to be 1410.2954 for $C_{57}H_{77}N_3O_{22}IS_4$;
c) Ultraviolet absorption spectrum: as shown in Figure III (methanol);
d) Infrared absorption spectrum: as shown in Figure IV (KBr disc);

N-acetyl-LL-E33288$\gamma_1^I$ e) Proton magnetic resonance spectrum: as shown in Figure V (300 MHz, CDCl$_3$);
f) Carbon-13 magnetic resonance spectrum: as shown in Figure VI (74.43 MHz, CDCl$_3$, ppm from TMS) significant peaks as listed below:

| | | | | | |
|---|---|---|---|---|---|
| 14.0 q | 17.6 q | 17.7 q | 19.0 q | 22.4 q | 22.8 q |
| 25.4 q | 36.7 t | 36.9 t | 39.2 t | 47.6 t | 51.6 d |
| 52.4 q | 53.1 t | 57.0 q | 57.2 q | 58.8 t | 60.9 q |
| 61.7 q | 64.4 d | 67.0 d | 68.1 d | 68.4 d | 69.0 d |
| 69.1 d | 70.5 d | 71.1 d | 71.7 s | 71.9 d | 72.4 d |
| 77.6 d | 80.8 d | 83.2 s | 87.0 d | 93.5 s | 97.9 d |
| 98.1 s | 99.7 d | 100.9 s | 101.3 d | 102.6 d | 123.2 d |
| 124.5 d | 127.1 d | 130.2 s | 133.4 s | 136.5 s | 142.9 s |
| 143.0 s | 150.6 s | 151.5 s | 155.0 s | 172.3 s | 191.9 s |
| 192.1 s | | | | | |

N-acetyl-dihydro-LL-E33288$\gamma_1^I$ a) Ultraviolet absorption spectrum: as shown in Figure VII (methanol);
b) Proton magnetic resonance spectrum: as shown in Figure VII (300 MHz, CDCl$_3$).

The N-acyl derivatives of the LL-E33288 antitumor antibiotics are most conveniently characterized by high-performance liquid chromatography (HPLC) and by thin-layer chromatography (TLC).

The preferred analytical HPLC system for the characterization of some of the N-acyl derivatives of the LL-E33288 antitumor antibiotics is shown below:

Column: Analytichem Sepralyte $C_{18}$,5$\mu$, 4.6 mm ×25 cm
Mobile Phase: 0.2M aqueous ammonium acetate, pH 6.0: acetonitrile, 50:50
Flow Rate: 1.5 ml/minute
Detection: UV$_{254nm}$ and UV$_{280nm}$ Table III gives the approximate retention times of some of the N-acyl derivatives of the LL-E33288 antitumor antibiotics:

TABLE III

| N-acyl-LL-E33288 Antitumor Antibiotics | Retention Time (minutes) |
|---|---|
| N-acetyl-LL-E33288$\gamma_1^I$ | 6.6 |
| N-formyl-LL-E33288$\gamma_1^I$ | 6.2 |
| N-acetyl-LL-E33288$\delta_1^I$ | 4.5 |
| N-formyl-LL-E33288$\delta_1^I$ | 4.2 |
| LL-E33288$\gamma_1^I$ | 8.0 |
| LL-E33288$\delta_1^I$ | 6.0 |

The preferred TLC system for the characterization of the N-acyl derivatives of the LL-E33288 antitumor antibiotics is shown below:

Adsorbent: Whatman High Performance TLC (HPTLC) plates, type LHP-KF;
Detection: Visualized by quenching effect under short wavelength UV lamp (254 nm);
Solvent System: Ethyl acetate saturated with 0.1M aqueous phosphate buffer at pH 7.0.

Table IV gives the approximate Rf values of some of the N-acyl derivatives of the LL-E33288 antitumor antibiotics in the TLC system above:

TABLE IV

| N-acyl-LL-E33288 Antitumor Antibiotics | Rf |
|---|---|
| N-acetyl-LL-E33288$\gamma_1^I$ | 0.53 |
| N-formyl-LL-E33288$\gamma_1^I$ | 0.53 |
| N-acetyl-LL-E33288$\delta_1^I$ | 0.25 |
| N-formyl-LL-E33288$\delta_1^I$ | 0.31 |
| N-acetyl-dihydro-LL-E33288$\gamma_1^I$ | 0.38 |
| N-monomethylsuccinyl-LL-E33288$\gamma_1^I$ | 0.42 |
| LL-E33288$\gamma_1^I$ | 0.25 |
| LL-E33288$\delta_1^I$ | 0.14 |

The N-acyl derivatives of the LL-E33288 antitumor antibiotics are useful as antibacterial agents. The in vitro antibacterial activity of N-acetyl-LL-E33288$\delta_1^I$, N-formyl-LL-E33288$\delta_1^I$ and N-acetyl-LL-E33288$\gamma_1^I$ was determined against a spectrum of gram-positive and gram-negative bacteria by a standard agar dilution method. Mueller-Hinton agar containing two-fold decreasing concentrations of the antibiotics was poured into petri plates. The agar surfaces were inoculated with 1 to 5×10$^4$ colony forming units of bacteria by means of a Steers replicating device. The lowest concentration of N-acyl-LL-E33288 antitumor antibiotic that inhibited growth of a bacterial strain after about 18 hours of incubation at approximately 35° C. was recorded as the minimal inhibitory concentration (MIC) for that strain. The results are summarized in Table V.

TABLE V

| | In vitro Antibacterial Activity of N-Acyl-LL-E33288 Antibiotics | | | |
|---|---|---|---|---|
| | | Minimal Inhibitory Concentration, mcg/ml | | |
| Organism* | | N-acetyl-LL-E33288$\delta_1^I$ | N-formyl-LL-E33288$\delta_1^I$ | N-acetyl-LL-E33288$\gamma_1^I$ |
| Escherichia coli | CMC 84-11 | 2 | 2 | >2 |
| Escherichia coli | No. 311 (MP) | 2 | 1 | >2 |
| Escherichia coli | ATCC 25922 | 1 | 1 | >2 |
| Klebsiella pneumoniae | CMC 84-5 | 8 | 4 | >2 |

TABLE V-continued

In vitro Antibacterial Activity of N-Acyl-LL-E33288 Antibiotics

| | | Minimal Inhibitory Concentration, mcg/ml | | |
|---|---|---|---|---|
| Organism | | N-acetyl-LL-E33288$\delta_1^I$ | N-formyl-LL-E33288$\delta_1^I$ | N-acetyl-LL-E33288$\gamma_1^I$ |
| *Klebsiella pneumoniae* | AD (MP) | 1 | 1 | 2 |
| *Enterobacter cloacae* | CMC 84-4 | 4 | 4 | >2 |
| *Serratia marcescens* | F-35 (MP) | 8 | 4 | >2 |
| *Pseudomonas aeruginosa* | 12-4-4 (MP) | 4 | 2 | >2 |
| *Pseudomonas aeruginosa* | ATCC 27853 | 4 | 2 | >2 |
| *Staphylococcus aureus* | Smith (MP) | 0.12 | 0.06 | 0.008 |
| *Staphylococcus aureus* | ATCC 25923 | 0.25 | 0.12 | 0.06 |
| *Staphylococcus epidermidis* | ATCC 12228 | 0.015 | 0.03 | 0.12 |
| *Streptococcus faecalis* | ATCC 29212 | 0.06 | 0.06 | 0.12 |
| *Streptococcus faecalis* | IO 83-28 | 0.5 | 0.12 | 0.12 |

The N-acyl derivatives of the LL-E33288 antitumor antibiotics are also active as antitumor agents as determined in the Biochemical Induction Assay (BIA), a bacterial assay system which specifically measures the ability of an agent to directly or indirectly initiate DNA damage. The indicator organism for this test is an *E. colilambda* lysogen, genetically constructed such that a DNA damaging event results in the expression of the gene for the enzyme $\beta$-glactosidase. This enzyme can be determined qualitatively or quantitatively by a biochemical assay as an indication that DNA damage has occurred.

A modified version of the quantitative liquid BIA disclosed by Elespuru, R. and Yarmolinsky, M., Environmental Mutagenesis, 1, 65 (1979) was used to evaluate these compounds.

Certain in vivo testing systems and protocols have been developed by the National Cancer Institute for testing compounds to determine their suitability as antineoplastic agents. These have been reported in "Cancer Chemotherapy Reports", Part III, Vol. 3, No. 2 (1972), Geran, et. al. These protocols have established standardized screening tests which are generally followed in the field of testing for anti-tumor agents. Of these systems, lymphocytic leukemia P388, melanotic melanoma B16 and colon 26 adenocarcinoma are particularly significant to the present invention. These neoplasms are utilized for testing as transplantable tumors in mice. Generally, significant anti-tumor activity, shown in these protocols by a percentage increase of mean survival times of the treated animals (T) over the control animals (C), is indicative of similar results against human leukemias and solid tumors.

Lymphocytic Leukemia P388 Test

The animals used were BDF$_1$ mice, all of one sex, weighing a minimum of 17 g and all within a 3 g weight range. There were 5 or 6 mice per test group. The tumor transplant was by intraperitoneal injection of 5 ml of dilute ascitic fluid containing $10^6$ cells of lymphocytic leukemia P388. The test compounds were administered intraperitoneally in a volume of 0.5 ml of 0.2% Klucel in normal saline on days 1, 5 and 9 (relative to tumor inoculation) at the indicated doses. The mice were weighed and the survivors recorded on a regular basis for 30 days. The median survival time and the ratio of survival time for treated (T)/control (C) animals were calculated. The parent antitumor antibiotic, LL-E33288$\gamma_1^I$, was used as positive control.

The test results of N-acetyl-LL-E33288$\gamma_1^I$, N-formyl-LL-E33288$\delta_1^I$ and N-acetyl-LL-E33288$\gamma_1^I$ are summarized in Table VI. If T/C×100 (%) is 125 or over, the tested compound is considered to have significant anti-tumor activity.

TABLE VI

| Lymphocytic Leukemia P388 Test | | | |
|---|---|---|---|
| Compound | Dose (mg/Kg) | Median survival (days) | T/C × 100 (%) |
| saline | | 11.0 | |
| N-acetyl-LL-E33288$\delta_1^I$ | 0.1 | 13.0 | 118 |
| | 0.05 | 29.5 | 268 |
| | 0.025 | 26.0 | 236 |
| | 0.0125 | 20.0 | 182 |
| | 0.006 | 20.0 | 182 |
| N-acetyl-LL-E33288$\delta_1^I$ | 0.1 | 11.5 | 105 |
| | 0.05 | 30.0 | 273 |
| | 0.025 | 25.0 | 227 |
| | 0.0125 | 23.0 | 209 |
| | 0.006 | 19.5 | 177 |
| N-formyl-LL-E33288$\delta_1^I$ | 0.1 | 12.5 | 114 |
| | 0.05 | 27.0 | 245 |
| | 0.025 | 22.5 | 205 |
| | 0.0125 | 21.0 | 191 |
| | 0.006 | 20.5 | 186 |
| LL-E33288$\gamma_1^I$ | 0.01 | 13.0 | 118 |
| | 0.005 | 25.0 | 227 |
| | 0.0025 | 30.0 | 273 |
| | 0.00125 | 26.5 | 241 |
| saline | | 11.0 | |
| N-acetyl-LL-E33288$\gamma_1^I$ | 0.08 | 18 | 164 |
| | 0.04 | 29.5 | 268 |
| | 0.02 | 28.0 | 255 |
| | 0.005 | 17.5 | 159 |
| | 0.0025 | 14.0 | 127 |
| | 0.00125 | 13.5 | 123 |
| LL-E33288$\gamma_1^I$ | 0.01 | 22.5 | 205 |
| | 0.005 | 26.0 | 236 |
| | 0.0025 | 24.5 | 223 |
| | 0.00125 | 21.0 | 191 |
| | 0.0006 | 19.0 | 173 |

Melanotic Melanoma B16 Test

The animals used were BDF$_1$ mice, all of the same sex, weighing a minimum of 17 g and all within a 3 g weight range. There are normally 6 animals per test group. A 1 g portion of melanoma B16 tumor was homogenized in 10 ml of cold balanced salt solution and a 0.5 ml aliquot of the homogenate was implanted intraperitoneally into each of the test mice. The test compounds were administered intraperitoneally on days 1 through 9 (relative to tumor inoculation) at various doses. The mice were weighed and survivors recorded on a regular basis for 60 days. The median survival time and the ratio of survival time for treated (T)/control (C)

animals was calculated. The parent antitumor antibiotic LL-E33288$\gamma_1^I$ was used as positive control.

The test results of N-acetyl-LL-E33288$\delta_1^I$ and N-acetyl-LL-E33288$\gamma_1^I$ are summarized in Table VII. If T/C×100 (%) is 125 or over, the tested compound is considered to have significant anti-tumor activity.

TABLE VII

Melanotic Melanoma B16 Test

| Compound | Dose (mg/Kg) | Median survival (days) | T/C × 100 (%) |
|---|---|---|---|
| saline | | 21.0 | |
| N-acetyl-LL-E33288$\delta_1^I$ | 0.025 | 35.5 | 169 |
| | 0.0125 | 27.5 | 131 |
| | 0.006 | 26.0 | 124 |
| | 0.003 | 25.0 | 119 |
| | 0.0015 | 21.5 | 102 |
| LL-E33288$\gamma_1^I$ | 0.0025 | 39.0 | 186 |
| | 0.00125 | 39.0 | 186 |
| | 0.0006 | 35.0 | 167 |
| | 0.0003 | 29.5 | 140 |
| | 0.00015 | 24.5 | 117 |
| saline | | 21.0 | |
| N-acetyl-LL-E33288$\gamma_1^I$ | 0.025 | 26.0 | 124 |
| | 0.0125 | 38.0 | 181 |
| | 0.006 | 39.0 | 186 |
| | 0.003 | 33.5 | 160 |
| | 0.0015 | 26.5 | 126 |
| | 0.00035 | 24.5 | 116 |
| | 0.00017 | 23.5 | 112 |
| LL-E33288$\gamma_1^I$ | 0.005 | 8.0 | 38 |
| | 0.0025 | 27.0 | 129 |
| | 0.00125 | 41.5 | 198 |
| | 0.0006 | 45.0 | 214 |
| | 0.0003 | 35.5 | 169 |
| | 0.00015 | 35.0 | 167 |
| | 0.00007 | 34.5 | 164 |
| | 0.00003 | 31 | 148 |

Colon 26 Adenocarcinoma Test

The animals used were CD$_2$F$_1$ female mice weighing a minimum of 17 g and all within a 3 g weight range. There were 5 or 6 mice per test group with three groups of 5 or 6 animals used as untreated controls for each test. The tumor implant was by intraperitoneal injection of 0.5 ml of a 2% colon 26 tumor brei in Eagle's MEM medium containing antibacterial agent. The test compounds were administered intraperitoneally on days 1, 5 and 9 (relative to tumor implant doses). The mice were weighed and deaths recorded on a regular basis for 30 days. The median survival times for treated (T)/control (C) animals were calculated. The parent antitumor antibiotic LL-E33288$\gamma_1^I$ was used as positive control.

The test results of N-acetyl-LL-E33288$\delta_1^I$ are summarized in Table VIII. If T/C×100 (%) is 130 or over, the tested compound is considered to have significant antitumor activity.

TABLE VIII

Colon 26 Adenocarcinoma Test

| Compound | Dose (mg/Kg) | Median survival (days) | T/C × 100 (%) |
|---|---|---|---|
| saline | | 16.0 | |
| N-acetyl-LL-E33288$\delta_1^I$ | 0.05 | 22.5 | 141 |
| | 0.025 | 40.0 | 250 |
| | 0.0125 | 21.0 | 131 |
| | 0.006 | 24.5 | 153 |
| | 0.003 | 19.0 | 119 |
| | 0.0015 | 19.0 | 119 |
| | 0.0007 | 19.0 | 119 |
| LL-E33288$\gamma_1^I$ | 0.01 | 14.0 | 88 |
| | 0.005 | 35.0 | 219 |
| | 0.0025 | 21.5 | 134 |
| | 0.00125 | 24.0 | 150 |
| | 0.0006 | 19.5 | 122 |
| | 0.0003 | 18.0 | 113 |
| | 0.00015 | 17.5 | 109 |

The invention is further described by the following non-limiting examples.

EXAMPLE 1

Preparation and purification of N-acetyl-LL-E33288$\delta_1^I$

Acetic anhydride (2 ml) was added dropwise to a stirred methanolic solution of partially purified LL-E33288$\delta_1^I$ (608 I mg, 57% pure, in 60 ml) cooled in an ice-water bath. The reaction mixture was allowed to stir at 0° C. for 1 hour, then warmed slowly to room temperature and the reaction was allowed to continue for another 3 hours. The reaction mixture was then concentrated in vacuo and the residue was taken up in a mixture of 60 ml each of dichloromethane and water. The aqueous phase was neutralized with dilute aqueous sodium hydroxide in order to remove as much of the acetic acid from the organic phase as possible. The organic phase was separated, dried over anhydrous sodium sulfate, concentrated to a small volume and was precipitated by addition of hexanes to give 604 mg of crude N-acetyl-LL-E33288$\delta_1^I$.

The crude N-acetyl-LL-E33288$\delta_1^I$ above was dissolved in 8 ml of acetonitrile:0.2M ammonium acetate, pH 6.0 (35:65) and was chromatographed in four batches on a Sepralyte C$_{18}$ column (1.5×21 cm). The columns were eluted at 10 ml/min. first with acetonitrile: 0.2M ammonium acetate pH 6.0 (35:65) for 30 minutes followed by a linear gradient to acetonitrile:0.2M ammonium acetate, pH 6.0 (40:60) over 60 minutes. Throughout the chromatography the column eluents were monitored at UV$_{254\ nm}$ and fractions were collected every 2.5 minutes. Peak fractions were analyzed by HPLC and those containing pure N-acetyl-LL-E33288$\delta_1^I$ according to the HPLC analysis were pooled and concentrated in vacuo to remove acetonitrile. The N-acetyl-LL-E33288$\delta_1^I$ present in the aqueous mixture was extracted into ethyl acetate and the ethyl acetate phase was dried over anhydrous sodium sulfate, concentrated to a small volume and was precipitated by addition of hexanes to give 161 mg of semi-purified N-acetyl-LL-E33288$\delta_1^I$.

TLC analysis (E. Merck Silica gel 60 F$_{254}$ precoated aluminum sheets, 0.2 mm, 3% isopropanol in ethyl acetate saturated with 0.1 M potassium dihydrogen phosphate, detected by bioautography using the agar biochemical induction assay) showed that the semi-purified N-acetyl-LL-E33288$\delta_1^I$ sample from above contained trace amounts of unreacted LL-E33288$\delta_1^I$. The semi-purified N-acetyl-LL-E33288$\delta_1^I$ (160 mg) was dissolved in 1 ml of ethyl acetate and chromatographed on a Bio-Sil A (20-44 μ, Bio-Rad Laboratories) column (1.5 cm×90 cm) packed and equilibrated with ethyl acetate. The column was first eluted with ethyl acetate at a flow rate of 3.6 ml/minute for 3.5 hours, collecting 18 ml fractions. The eluent was changed to 3% isopropanol in ethyl acetate saturated with 0.1 M potassium dihydrogen phosphate and elution continued for another 3.5 hours. The fractions were analyzed by TLC as before and those contain pure N-acetyl-LL-E33288$\delta_1^I$ (fractions 58-64) were pooled, concentrated in vacuo to dryness, redissolved in a small amount of ethyl acetate and was precipitated by addition of hexanes to give 118 mg of analytically pure N-acetyl-LL-E33288$\delta_1^I$, containing no detectable amounts of the un-acylated parent antitumor antibiotic. The proton magnetic resonance spectrum is shown in Figure I.

EXAMPLE 2

Preparation and purification of N-formyl-LL-E33288$\delta_1^I$

The mixed anhydride of acetic acid and formic acid was freshly prepared by addition of 200 μl of formic acid dropwise to 400 μl of acetic anhydride cooled in an ice water bath. The reaction mixture was then warmed at 50° C. for 5 minutes to complete the anhydride exchange and was then kept at 0° C. The mixed anhydride of acetic acid and formic acid (100 μl) prepared above was added dropwise to a stirred methanolic solution of partially purified LL-E33288$\delta_1^I$ (92 mg, 45% pure, in 30 ml) cooled in an ice-water bath. The reaction mixture was allowed to stir at 0° C. for 45 minutes, hexanes (20 ml) was then added to the reaction mixture and the mixture was concentrated in vacuo to mean dryness. The residue was redissolved in ethyl acetate and precipitated by addition of hexanes to give a chunky, sticky precipitate which was collected by centrifugation. The precipitate was redissolved in a small amount of ethyl acetate and precipitated again by addition of hexanes to give crude N-formyl-LL-E33288$\delta_1^I$.

The crude N-formyl-LL-E33288$\delta_1^I$ sample from above was partially purified by preparative TLC on silica gel (two of Analtech Silica Gel GF precoated plates, 2,000 μ, 20×20 cm) eluting with ethyl acetate saturated with phosphate buffer at pH 7.0. The desired band was excised and the N-formyl-LL-E33288$\delta_1^I$ was recovered by washing the silica gel with methylene chloride: methanol (80:20) to give, upon workup, 110 mg of partially purified N-formyl-LL-E33288$\delta_1^I$.

The partially purified N-formyl-LL-E33288$\delta_1^I$ from above was dissolved in 1 ml of acetonitrile:ammonium acetate, pH 6.0 (35:65) and was chromatographed on a Sepralyte $C_{18}$ column (1.5×20 cm). The column was eluted at 8 ml/minute with acetonitrile:0.2M ammonium acetate, pH 6.0 (35:65) for 1.75 hours, monitoring at $UV_{254nm}$ and collecting 20 ml fractions. Peak fractions were analyzed by HPLC and those containing pure N-formyl-LL-E33288$\delta_1^I$ according to the HPLC analysis were pooled and concentrated in vacuo to remove acetonitrile. The cloudy aqueous mixture, containing N-formyl-LL-E33288$\delta_1^I$ was extracted with ethyl acetate and the ethyl acetate phase was concentrated to dryness. The residue was redissolved in methylene chloride, dried over anhydrous sodium sulfate, concentrated and precipitated by addition of hexanes to give 36.5 mg of semi-purified N-formyl-LL-E33288$\delta_1^I$.

TLC analysis (E. Merck Silica gel 60 F254 precoated aluminium sheets, 0.2 mm, 3% isopropanol in ethyl acetate saturated with 0.1 M potassium hydrogen phosphate, detected by bioautography using the agar biochemical induction assay) showed that the semi-purified N-formyl-LL-E33288$\delta_1^I$ sample above contained trace amounts of unreacted LL-E33288$\delta_1^I$ and $\gamma_1^I$. The semipurified N-formyl-LL-E33288$\delta_1^I$ (36.5 mg) was dissolved in 1 ml of ethyl acetate and chromatographed on a Bio-Sil A (20-44 μ, Bio-Rad Laboratories) column (1.5 cm×23 cm) packed and equilibrated with ethyl acetate. The column was first eluted with ethyl acetate at a flow rate of 1.2 ml/minute for 2 hours, collecting 6 ml fractions. The eluent was changed to ethyl acetate:-methanol (97:3) and elution continued for another 2 hours. The fractions were analyzed by TLC (E. Merck Silica gel 60 F254 precoated aluminium sheets, 0.2 mm, 3% isopropanol in ethyl acetate saturated with 0.1 M potassium hydrogen phosphate, detected by spraying with a solution of 3% cupric acetate in 8% aqueous phosphoric acid) and those contained pure N-formyl-LL-E33288$\delta_1^I$ (fractions 35-38) were pooled, concentrated in vacuo to dryness. The residue was redissolved in a small amount of ethyl acetate, and precipitated by addition of hexanes to give an N-acetyl-LL-E33288$\delta_1^I$ sample which was still contaminated with trace amount of unreacted LL-E33288$\gamma_1^I$. This sample was chromatographed again on a Bio-Sil A column (0.8×20 cm) packed and equilibrated with ethyl acetate. The column was eluted with ethyl acetate at a flow rate of 1.2 ml/minute for 4 hours, collecting 6 ml fractions. The fractions were analyzed by TLC as before and those contained pure N-formyl-LL-E33288$\delta_1^I$ (fractions 14-33) were pooled and worked up as before to give 12.2 mg of analytically pure N-formyl-LL-E33288$\delta_1^I$, containing no detectable amounts of the un-acylated parent antibiotic. The proton magnetic resonance spectrum is displayed in Figure II.

EXAMPLE 3

Preparation and purification of N-formyl-LL-E33288$\delta_1^I$

The mixed anhydride of acetic acid and formic acid (750 μl) freshly prepared as described in Example 2 was added dropwise to a stirred methanolic solution of partially purified LL-E33288$\delta_1^I$ (689 mg, 70% pure, in 150 ml) cooled in an ice-water bath. The reaction mixture was allowed to stir at 0° C. for one hour, excess hexanes was then added to the reaction mixture and the mixture was concentrated in vacuo to about 75 ml. Ethyl acetate (about 200 ml) was added to the solution and the mixture was concentrated to about 50 ml and crude N-formyl-LL-E33288$\delta_1^I$ (676 mg) was precipitated by addition of 300 ml of hexanes.

The crude N-formyl-LL-E33288$\delta_1^I$ was dissolved in 3 ml of ethyl acetate and chromatographed on a Bio-Sil A (40-80 μ) column (2.5×95 cm) packed and equilibrated in ethyl acetate. The column was eluted at 10 ml/min with ethyl acetate until the yellow band was off the column (1.75 hours). It was then eluted at 5 ml/min with ethyl acetate saturated with 0.1 M potassium dihydrogen phosphate for another 5 hours. Throughout the chromatography 20 ml fractions were collected. The fractions were analyzed by TLC (E. Merck Silica gel 60 F254 precoated aluminium sheets, 0.2 mm, 3% isopropanol in ethyl acetate saturated with 0.1 M potassium dihydrogen phosphate, detected by spraying with a solution of 3% cupric acetate in 8% aqueous phosphoric acid) and the major N-formyl-LL-E33288$\delta_1^I$ containing fractions (92-98) were pooled and worked up by concentration and precipitation to give 294 mg of partially purified N-formyl-LL-E33288$\delta_1^I$. TLC analysis (detected by bioautography using the agar biochemical induction assay) of this sample showed it to be free of any unreacted LL-E33288$\delta_1^I$.

The partially purified N-formyl-LL-E33288$\delta_1^I$ was dissolved in 4 ml of acetonitrile:0.2M ammonium acetate, pH 6.0 (35:65) and was chromatographed in two batches on a Sepralyte $C_{18}$ column (1.5×45 cm) equilibrated with acetonitrile:0.2M ammonium acetate, pH 6.0 (35:65). The column was eluted at 8 ml/min with the same solvent for 3 hours, monitoring at $UV_{254nm}$ and collecting 20 ml fractions. Peak fractions were analyzed by HPLC and those containing pure N-formyl-LL-E33288$\delta_1^I$ according to the HPLC analysis were pooled and concentrated in vacuo to remove acetonitrile. The N-formyl-LL-E33288$\delta_1^I$ present in the aqueous mixture was extracted into ethyl acetate and worked up by concentration and precipitation to give 161 mg of pure N-formyl-LL-E33288$\delta_1^I$. The proton magnetic resonance spectrum is displayed in Figure II.

EXAMPLE 4

Preparation of N-acetyl-LL-E33288$\gamma_1^I$

Acetic anhydride (4 ml) was added dropwise to a stirred methanolic solution of partially purified LL-E33288$\gamma_1^I$ (1.25 g, 85% pure, in 100 ml of methanol) cooled in an ice-water bath. The reaction mixture was allowed to stir at 0° C. for 1 hour, then warmed slowly to room temperature and the reaction was allowed to continue for another 2 hours. The reaction mixture was then concentrated in vacuo and the residue was taken up in a mixture of 100 ml each of dichloromethane and water. The aqueous phase was neutralized with dilute aqueous sodium hydroxide in order to remove most of the acetic acid from the organic phase. The organic phase was separated, dried over anhydrous sodium sulfate, concentrated to a small volume and the product was precipitated by addition of hexanes to give 1.18 g of 80% pure N-acetyl-LL-E33288$\gamma_1^I$ which can be purified following procedures described in Example 1 to give pure N-acetyl-LL-E33288$\gamma_1^I$. The ultraviolet, infrared, proton and carbon-13 spectrums are displayed in Figures III-VI.

EXAMPLE 5

Preparation of N-formyl-LL-E33288$\gamma_1^I$

The mixed anhydride of acetic acid and formic acid (100 μl) freshly prepared as described in Example 2 was added dropwise to a stirred methanolic solution of analytically pure LL-E33288$\gamma_1^I$ (49.6 mg, in 50 ml of methanol) cooled in an ice-water bath. The reaction mixture was allowed to stir at 0° C. for one hour followed by at room temperature overnight. It was then concentrated to dryness, redissolved in a small volume of ethyl acetate and the product was precipitated by addition of hexane. The dried precipitate was redissolved in 10 ml of methanol and treated again with the mixed anhydride of acetic acid and formic acid (400 μl). The reaction mixture was allowed to stir at room temperature for 2 hours and was worked up by concentration and precipitation as described before to give crude N-formyl-LL-E33288$\gamma_1^I$ as an off-white solid. The crude N-formyl-LL-E33288$\gamma_1^I$ was purified by preparative TLC (two 20 cm×20 cm Analtech tapered Silica Gel GF plates, eluted with 3% isopropanol in ethyl acetate saturated with 0.1 M potassium dihydrogen phosphate) to give semi-purified N-formyl-LL-E33288$\gamma_1^I$.

EXAMPLE 6

Preparation of N-acetyl-dihydro-LL-E33288$\gamma_1^I$

A 2 ml portion of methyl iodide was added to a solution of 25 mg of N-acetyl-LL-E33288$\gamma_1^I$ (prepared as described in Example 4) in 8 ml of absolute ethanol and the mixture was cooled in an ice-water bath. To this was added one ml of a 0.4M ethanolic solution of sodium borohydride in two equal portions. When the reaction was complete (10 minutes after addition of the second portion of sodium borohydride solution), the borate complex was decomposed by the addition of 400 μl of a 4 M ethanolic solution of acetic acid. The reaction mixture was then concentrated to a golden yellow residue which was redissolved in 10 ml of ethyl acetate, diluted with 10 ml of dichloromethane and re-concentrated to dryness. This residue was redissolved in ethyl acetate, the insoluble borate salt was filtered off, and the solution was concentrated to dryness to give an off-white solid which was suspended in 4 ml of water and passed through a Bond Elut ™ (Analytichem International) $C_{18}$ cartridge. The cartridge was sequentially eluted with 4 ml each of water, methanol:water (1:1) and methanol. The methanol eluate, containing most of the N-acetyl-dihydro-LL-E33288$\gamma_1^I$, was concentrated to give an off-white solid and was further purified by preparative TLC (Analtech Silica Gel GF, 20×20 cm, 1000 μlayer thickness, ethyl acetate:methanol, 97:3 elution) to give analytically pure N-acetyl-dihydro-LL-E33288$\gamma_1^I$. The ultraviolet and proton magnetic resonance spectrum is displayed in Figures VII and VIII.

EXAMPLE 7

Preparation of N-monomethylsuccinyl-LL-E33288$\gamma_1^I$

The anhydride of the monomethyl ester of succinic acid (55 mg) was added in three portions to a solution of LL-E33288$\gamma_1^I$ (12.3 mg) in methanol (2 ml) and kept at room temperature for a three day period. The reaction mixture was concentrated to dryness and the residue was redissolved in a small volume of ethyl acetate and precipitated by addition of hexane. The gummy precipitate was triturated thoroughly with diethyl ether and was then redissolved in a small volume of ethyl acetate and precipitated by the addition of diethyl ether and hexane to give crude N-monomethylsuccinyl-LL-E33288$\gamma_1^I$.

I claim:
1. A compound of the formula

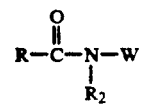

wherein
R is hydrogen or a branched or unbranched alkyl ($C_1$–$C_{10}$) optionally substituted by one or more hydroxy, or carboxy;
$R_2$ is $CH_3$, $C_2H_5$ or $CH(CH_3)_2$;
W is

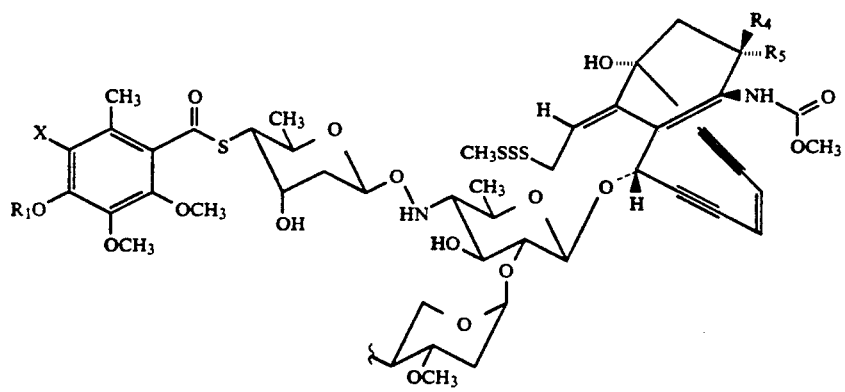

wherein
R₁ is H or

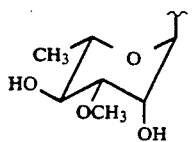

R₄ is OH when R₅ is H or
R₄ and R₅ taken together are a carbonyl; and X is an iodine or bromine atom.

2. A compound according to claim 1 of the formula:

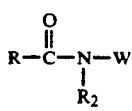

which is the antitumor antibiotic N-acetyl LL-E33288δ₁$^I$, wherein W is as defined in claim 1; R is CH₃; R₁ is

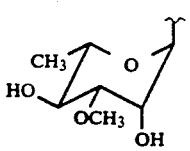

R₂ is CH₃; R₄ and R₅ taken together is a carbonyl; X is iodine and having:
a) a proton magnetic resonance spectrum as shown in Figure I;
b) a molecular weight of 1395 as determined by FABMS;
c) a molecular formula of C₅₆H₇₄N₃O₂₂IS₄ with an exact mass for M+K as determined by high resolution FAB-MS to be 1420.217 for C₅₆H₇₄N₃O₂.2IS₄K;
d) a retention time of 4.5 minutes by HPLC using a Analytichem Sepralyte C₁₈, 5u, 4,6 mm×25 cm column with a mobile phrase of 0.2 M aqueous ammonium acetate at pH 6.0 made 1:1 with acetonitrile and having a flow rate of 1.5 ml/minute with UV detection at 254 nm and 280 nm; and
e) a Rf of 0.25 on Whatman High Performance TLC (HPTLC) plates, type LHP-KF using ethyl acetate saturated with 0.1 M aqueous phosphate buffer at pH 7.0, visualized using a 254 nm UV lamp.

3. A compound according to claim 1 of the formula:

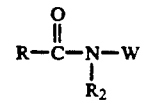

which is the antitumor antibiotic N-formyl LL-E33288δ₁$^I$, wherein W is as defined in claim 1; R is H; R₁ is

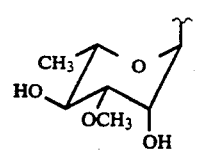

R₂ is CH₃; R₄ and R₅ taken together is a carbonyl; X is iodine and having:
a) a protonmagnetic resonance spectrum as shown in Figure II;
b) a molecular weight of 1381 as determined by FAB-MS;
c) a molecular formula of C₅₅H₇₂N₃O₂₂IS₄ with an exact mass for M+K as determined by high resolution FAB-MS to be 1420.2172 for C₅₅H₇₂N₃O₂.2IS₄K;
d) a retention time of 4.2 minutes by HPLC using an Analytichem Sepralyte C₁₈, 5u, 4.6 mm ×25 cm column with a mobile phase of 0.2 M aqueous ammonium acetate at pH 6.0, made 1:1 with acetonitrile and having a flow rate of 1.5 ml/minute with UV detection at 254 nm and 280 nm; and
e) a Rf of 0.31 on Whatman High Performance TLC (HPTLC) plates, Type LHP-KF using ethyl acetate saturated with 0.1 M aqueous phosphate buffer at pH 7.0, visualized using a 254 nm UV lamp.

4. A compound according to claim 1 of the formula:

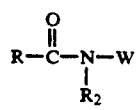

which is the antitumor antibiotic N-acetyl-LL-E33288δ$_1^I$, wherein W is as defined in claim 1; R is CH$_3$; R$_1$ is

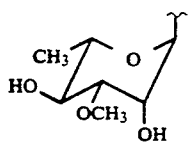

R$_2$ is C$_2$H$_5$; R$_4$ and R$_5$ taken together is a carbonyl; X is iodine and having:
 a) a ultraviolet spectrum as shown in Figure III;
 b) an infrared absorption spectrum as shown in Figure IV;
 c) a proton magnetic resonance spectrum as shown in Figure V; and
 d) a carbon-13 magnetic resonance spectrum as shown in Figure VI with significant peak listed as:

| | | | | | |
|---|---|---|---|---|---|
| 14.0 q | 17.6 q | 17.7 q | 19.0 q | 22.4 q | 22.8 q |
| 25.4 q | 36.7 t | 36.9 t | 39.2 t | 47.6 t | 51.6 d |
| 52.4 q | 53.1 t | 57.0 q | 57.2 q | 58.8 t | 60.9 q |
| 61.7 q | 64.4 d | 67.0 d | 68.1 d | 68.4 d | 69.0 d |
| 69.1 d | 70.5 d | 71.1 d | 71.7 s | 71.9 d | 72.4 d |
| 77.6 d | 80.8 d | 83.2 s | 87.0 s | 93.5 s | 97.9 d |
| 98.1 s | 99.7 d | 100.9 s | 101.3 d | 102.6 d | 123.2 d |
| 124.5 d | 127.1 d | 130.2 s | 133.4 s | 136.5 s | 142.9 s |
| 143.0 s | 150.6 s | 151.5 s | 155.0 s | 172.3 s | 191.9 s |
| 192.1 s | | | | | | e) a molecular weight of 1409 as determined by FAB-MS;
 f) a molecular formula of C$_{57}$H$_{76}$N$_3$O$_{22}$IS$_4$ with an exact mass for M+H as determined by high resolution FAB-MS to be 1410.2954 for C$_{57}$H$_{76}$N$_3$O$_{2\cdot 2}$IS$_4$;
 g) a retention time of 6.6 minutes by HPLC using an Analytichem Sepralyte C$_{18}$, 5u, 4.6 mm×25 cm column with a mobile phase of 0.2M aqueous ammonium acetate at pH 6.0, made 1:1 with acetonitrile and having a flow rate of 1.5 ml/minute with UV detection at 254 mm and 280 nm; and
 h) a Rf of 0.53 on Whatman High Performance TLC (HPTLC) plates, type LHP-KF using ethyl acetate saturated with 0.1 M aqueous phosphate buffer at pH 7.0, visualized using a 254 nm UV lamp.

5. A compound according to claim 1 of the formula:

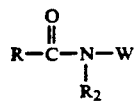

which is the antitumor antibiotic N-formyl-LL-E33288δ$_1^I$, wherein W is as defined in claim 1; R is H; R$_1$ is

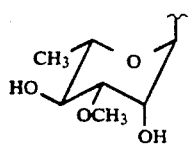

R$_2$ is C$_2$H$_5$; R$_4$ and R$_5$ taken together is a carbonyl; and X is iodine and having:
 a) a retention time of 6.2 minutes by HPLC using an Analytichem Sepralyte C$_{18}$, 5u, 4.6 mm×25 cm column with a mobile phase of 0.2M aqueous ammonium acetate at pH 6.0, made 1:1 with acetonitrile and having a flow rate of 1.5 ml/minute with UV detection at 254 nm and 280 nm; and
 b) a Rf of 0.53 on Whatman High Performance TLC (HPTLC) plates, Type LHP-KF using ethyl acetate saturated with 0.1 M aqueous phosphate buffer at pH 7.0, visualized using a 254 nm UV lamp.

6. A compound according to claim 1 of the formula:

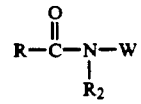

which is the antitumor antibiotic N-acetyl-dihydro-LL-333288γ$_1^I$, wherein W is as defined in claim 1; R is CH$_3$; R$_1$ is

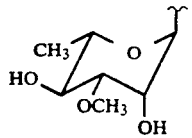

R$_2$ is C$_2$H$_5$; R$_4$ is H; X is iodine; and having
 a) a ultraviolet absorption spectrum as shown in Figure VII;
 b) a proton magnetic resonance spectrum as shown in Figure VIII, and
 c) a Rf of 0.38 on Whatman High Performance TLC (HPTLC) plates, type LHP-KF using ethyl acetate saturated with 0.1 M aqueous phosphate buffer at pH 7.0, visualized using a 254 nm UV lamp.

7. A compound according to claim 1 of the formula:

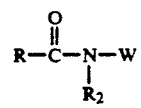

which is the antitumor antibiotic N-monomethyl-succinyl-LL-E33288γ$_1^I$, wherein W is as defined in claim 1; R is —CH$_2$CH$_2$CO$_2$CH$_3$; R$_1$ is

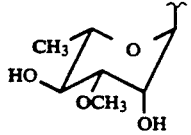

R$_2$ is C$_2$H$_5$; R$_4$ and R$_5$ taken together is a carbonyl; X is iodine; and having:
 a) a Rf of 0.42 on Whatman High Performance TLC (HPTLC) plates, type LHP-KF using ethyl acetate saturated with 0.1 M aqueous phosphate buffer at pH 7.0, visualized using a 254 nm UV lamp.

8. A process for producing a compound of the formula:

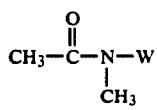

wherein W is

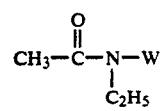

wherein W is

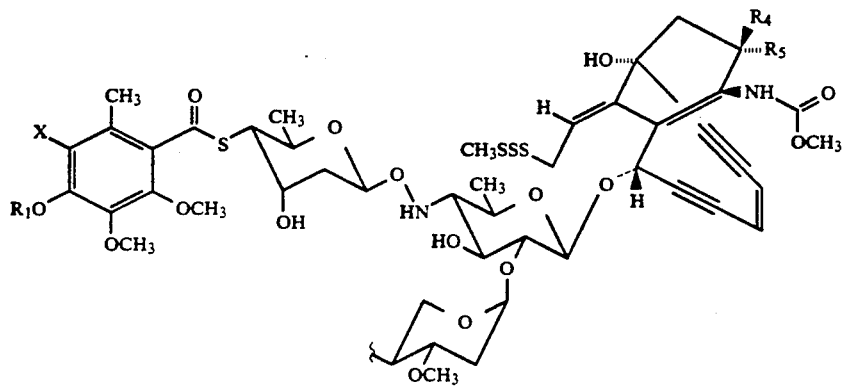

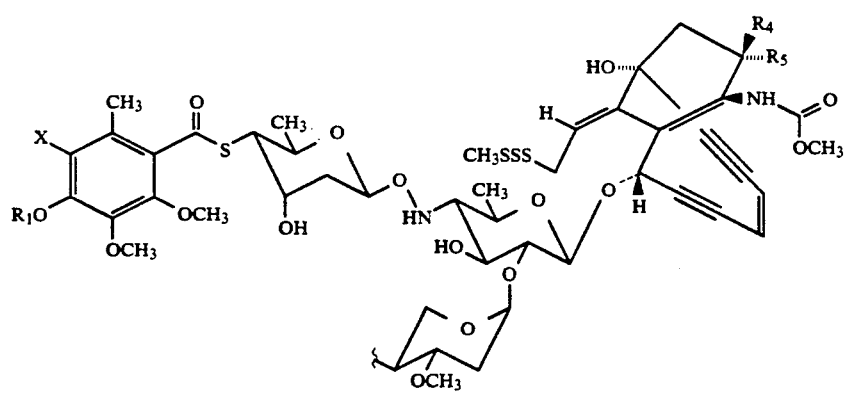

$R_1$ is H or

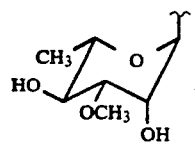

$R_4$ is OH when $R_5$ is H and x is an iodine or bromine atom comprising reacting

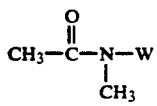

wherein W is as defined above except $R_4$ and $R_5$ are taken together to form a ketone with sodium borohydride in an alcoholic solution at $-5°$ C. to about $+5°$ C. from 5 minutes to 5 hours.

9. A process for producing a compound of the formula:

$R_1$ is H or

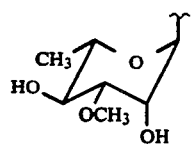

$R_4$ is OH when $R_5$ is H and X is an iodine or bromine atom comprising reacting

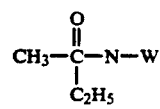

wherein W is as defined above except $R_4$ and $R_5$ are taken together to form a ketone with sodium borohydride in an alcoholic solution at $-5°$ C. to about $+5°$ C. from 5 minutes to 5 hours.

10. A process for producing a compound of the formula:

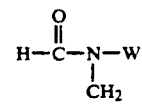

wherein W is

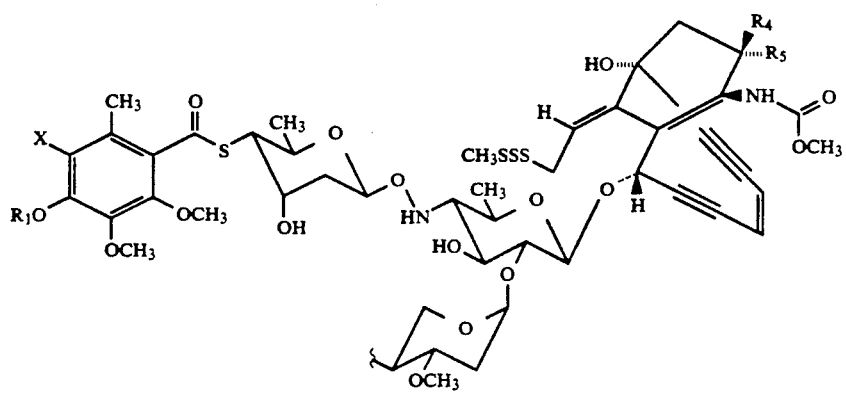

$R_1$ is H or

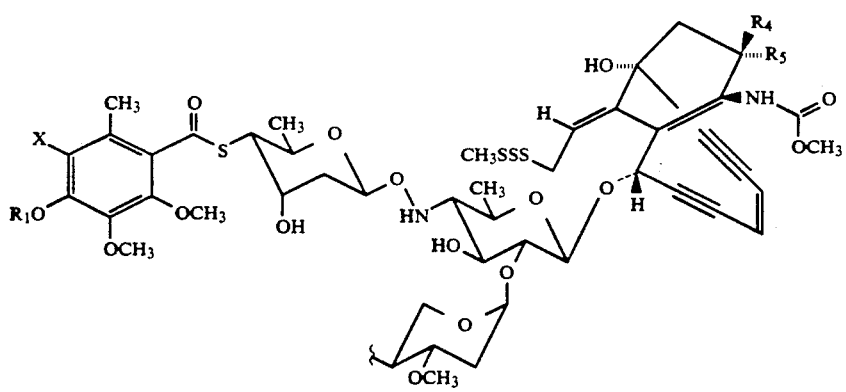

$R_1$ is H or wherein W is

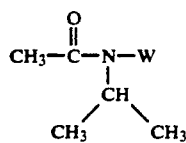

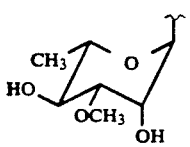

$R_4$ is OH or when $R_5$ is H and
X is an iodine or bromine atom comprising reacting

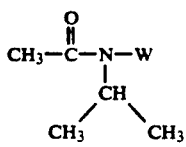

wherein w is as defined above except $R_4$ and $R_5$ are taken together to form a ketone with sodium borohydride in an alcoholic solution at $-5°$ C. to about $+5°$ C. from 5 minutes to 5 hours.

11. A process for producing a compound of the formula:

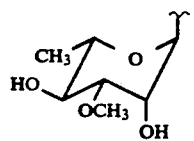

$R_4$ is OH when $R_5$ is H and
X is an iodine or bromine atom comprising reacting

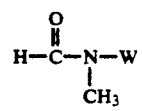

wherein W is as defined above except $R_4$ and $R_5$ are taken together to form a ketone with sodium borohydride in an alcoholic solution at $-5°$ C. to about $+5°$ C. from 5 minutes to 5 hours.

12. A process for producing a compound of the formula:

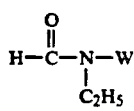

wherein W is

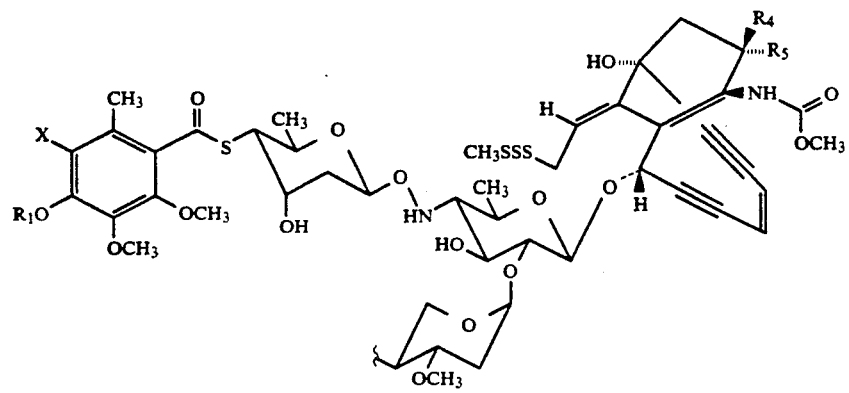

R₁ is H or

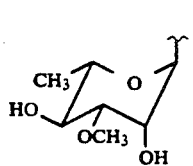

R₄ is OH when R₅ is H and
X is an iodine or bromine atom comprising reacting

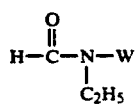

wherein W is as defined above except R₄ and R₅ are taken together to form a ketone with sodium borohydride in an alcoholic solution at −5° C. to about +5° C. from 5 minutes to 5 hours.

13. A process for producing a compound of the formula

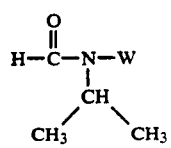

wherein W is

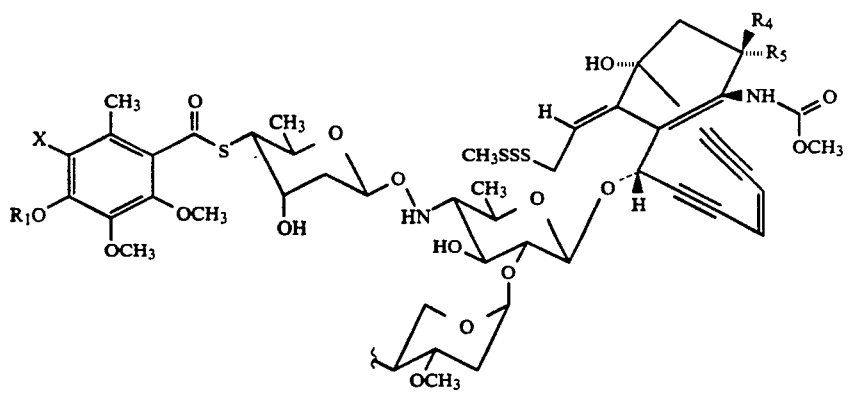

R₁ is H or

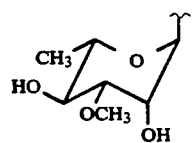

R₄ is OH when R₅ is H and
X is an iodine or bromine atom comprising reacting

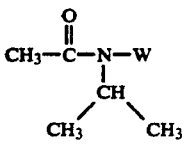

wherein W is as defined above except R₄ and R₅ are taken together to form a ketone with sodium borohydride in an alcoholic solution at −5° C. to about +5° C. from 5 minutes to 5 hours.

14. A process for producing a compound of the formula:

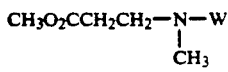

wherein W is

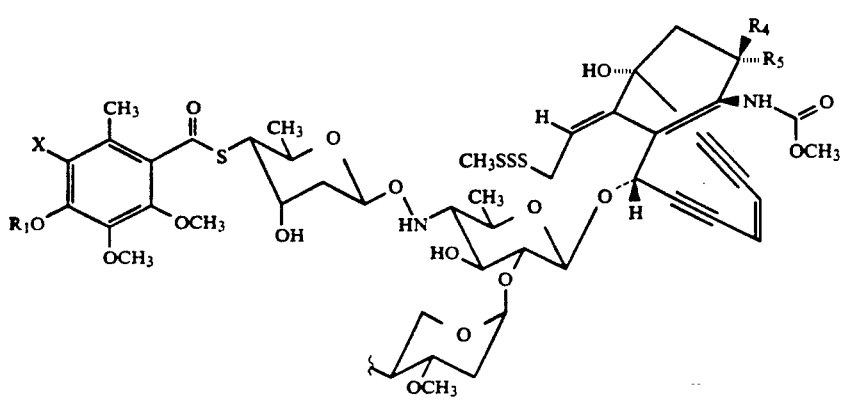

R₁ is H or

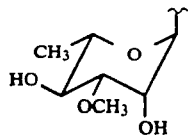

R₄ is OH when R₅ is H and
X is an iodine or bromine atom comprising reacting

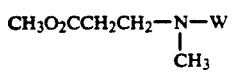

wherein W is as defined above except R₄ and R₅ are taken together to form a ketone with sodium borohydride in an alcoholic solution at −5° C. to about +5° C. from 5 minutes to 5 hours.

15. A process for producing a compound of the formula:

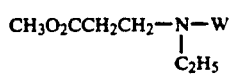

wherein W is

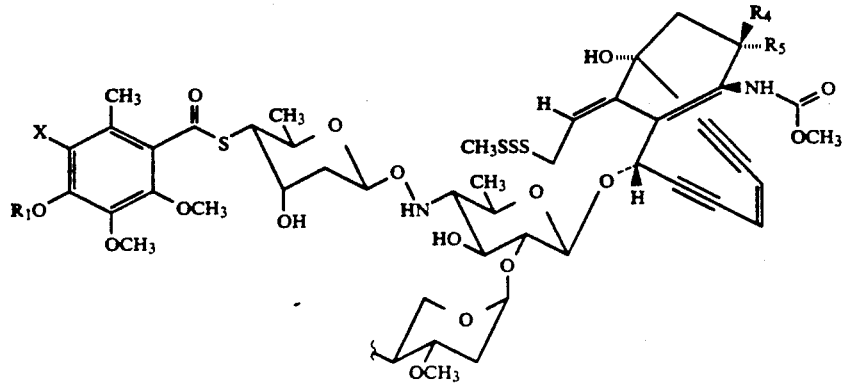

R₁ is H or

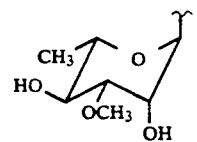

R₄ is OH when R₅ is H and
X is an iodine or bromine atom comprising reacting

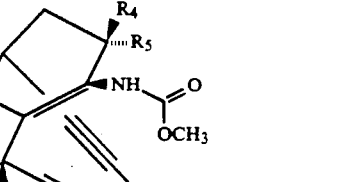

wherein W is as defined above except R₄ and R₅ are taken together to form a ketone with sodium borohydride in an alcoholic solution at −5° C. from 5 minutes to 5 hours.

16. A process for producing a compound of the formula:

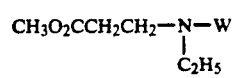

wherein W is

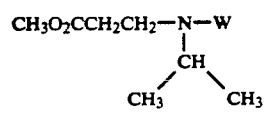

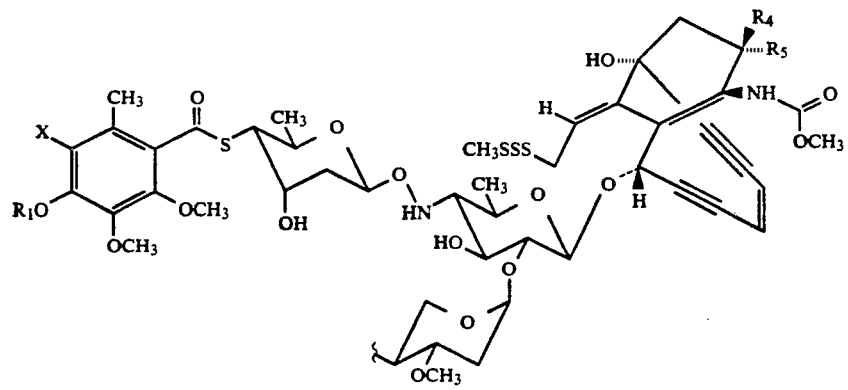

R₁ is H or

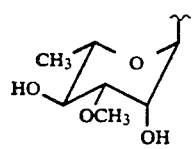

R₄ is OH when R₅ is H and
X is an iodine or bromine atom comprising reacting

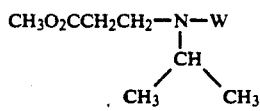

wherein W is as defined above except R₄ and R₅ are taken together to form a ketone with sodium borohydride in an alcoholic solution at $-5°$ C. to about $+5°$ C. from 5 minutes to 5 hours.

17. A method of treating bacterial infections in warm-blooded animals which comprises administering to said animals an antibacterially effective amount of a compound of the formula:

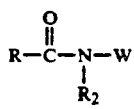

wherein W is

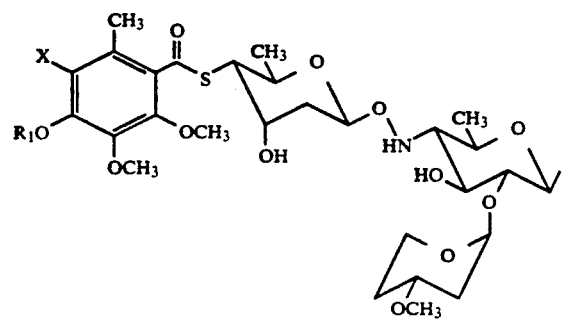

-continued

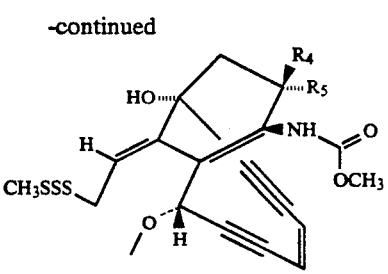

R is hydrogen or a branched or unbranched alkyl ($C_1$-$C_{10}$) optionally substituted by one or more hydroxy, or carboxy; R₁ is H or

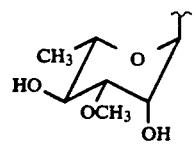

R₂ is $CH_3$, $C_2H_5$ or $CH(CH_3)_2$; R₄ is OH when R₅ is H or R₄ and R₅ taken together are a carbonyl; and X is an iodine or bromine atom.

18. A method of testing the growth of tumors in warm-blooded animals which comprises administering to said animals an oncolytic amount of a compound of the formula:

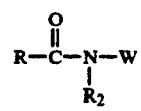

wherein W is

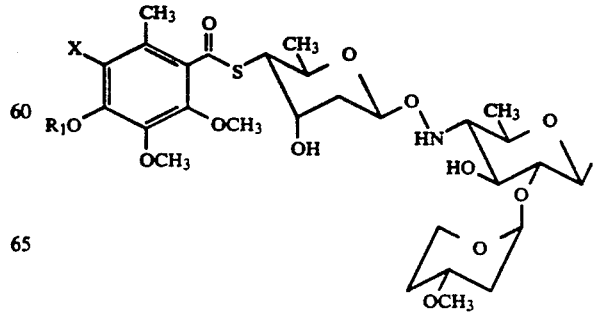

-continued
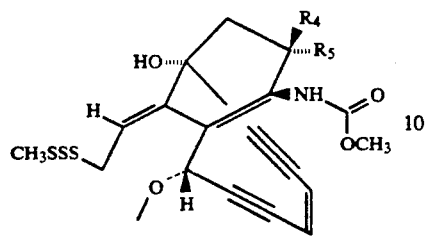
R is hydrogen or a branched or unbranched alkyl ($C_1$–$C_{10}$) optionally substituted by one or more hydroxy, or carboxy; $R_1$ is H or
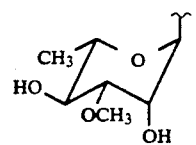
$R_2$ is $CH_3$, $C_2H_5$ or $CH(CH_3)_2$; $R_4$ is OH when $R_5$ is H or $R_4$ and $R_5$ taken together are a carbonyl; and X is an iodine or bromine atom.
* * * * *